United States Patent [19]

John et al.

[11] Patent Number: 5,504,230

[45] Date of Patent: Apr. 2, 1996

[54] PREPARATION OF 9-(Z)-RETINOIC ACID

[75] Inventors: Michael John, Ludwigshafen; Joachim Paust, Neuhofen, both of Germany

[73] Assignee: BASF Aktiengesellschaft, Ludwigshafen, Germany

[21] Appl. No.: 358,113

[22] Filed: Dec. 16, 1994

[30] Foreign Application Priority Data

Dec. 23, 1993 [DE] Germany .......................... 43 44 148.3

[51] Int. Cl.$^6$ .............................. C07C 51/00; C07F 9/02
[52] U.S. Cl. .......................... 554/154; 554/206; 554/207; 554/221; 568/9
[58] Field of Search ..................................... 884/221, 206, 884/207, 154; 568/9

[56] References Cited

U.S. PATENT DOCUMENTS 4,182,731  1/1980  Schulz et al. ................. 568/9

FOREIGN PATENT DOCUMENTS 000140  1/1979  European Pat. Off. .

OTHER PUBLICATIONS

Angew. Chem. 72, Nr. 22 (1960) pp. 811–819.
Nature 355 (1992) pp. 359–361.
Angew. Chem. 77 (1965) 277–360.
Agnew Chem. 80 (1968) 35–36.

Primary Examiner—José G. Dees
Assistant Examiner—Deborah D. Carr
Attorney, Agent, or Firm—Keil & Weinkauf

[57] ABSTRACT

A process for preparing 9-(Z)-retinoic acid from mother liquors from the industrial preparation of $C_{15}$-triarylphosphonium salts of the general formula I

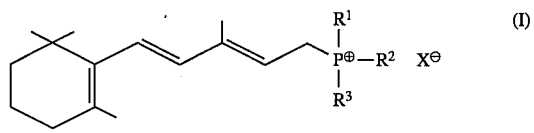

where $R^1$ to $R^3$ are each aryl and $X^\ominus$ is halogen or $(HSO_4)^\ominus$, in an organic solvent, which comprises A. increasing the proportion of 9-(Z)-$C_{15}$-triarylphosphonium salt in the $C_{15}$-triarylphosphonium salts isolated from the mother liquor by treatment with isopropanol at elevated temperature, cooling and separating off the all-(E)-$C_{15}$-triarylphosphonium salt which has crystallized out, B. subjecting the resulting $C_{15}$-triarylphosphonium salt to a Wittig reaction with an alkyl β-formylcrotonate of the general formula

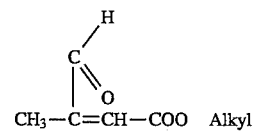

and C. hydrolyzing the resulting oily retinoic ester mixture in a $C_3$–$C_9$-alkanol, preferably in a propanol or butanol, precipitating the resulting 9-(Z)-retinoic acid where appropriate by adding methanol as crystals, with all-(E)-retinoic acid and other retinoic acid isomers remaining in the alkanolic solution.

13 Claims, No Drawings

PREPARATION OF 9-(Z)-RETINOIC ACID

BACKGROUND OF THE INVENTION

1. Field of the Invention 9-(Z)-Retinoic acid is a substance of physiological importance (cf. Nature 355 (1992) 359–361). It has a high binding affinity for the nuclear retinoic acid acceptor $RXR_\alpha$ which is also activated by direct ligand interaction. This interaction has been observed to result in altered gene expression, which makes it possible substantially to influence cellular processes.

Since no utilizable process for the preparation of 9-(Z)-retinoic acid is known to date, it was an object of the invention to develop an advantageous process for its preparation.

2. Description of the Art

The retinoic acid isomer which has been used most commonly to date, all-(E)-retinoic acid, is advantageously prepared by Wittig reaction of a β-ionylideneethyltriphenylphosphonium salt ($C_{15}$-triphenylphosphonium salt) with a β-formylcrotonic ester. Subsequent separation of the resulting double-bond isomers is possible only with extremely elaborate preparative chromatographic methods.

In the preparation of the $C_{15}$-triphenylphosphonium salt required for industrial vitamin A syntheses and for preparing other vitamin A derivatives, such as retinal and retinoic acid, (see, for example, H. Pommer et al. in Angew. Chem. 77 (1965) 277–360) the mother liquor after removal of the required product contains, besides all-(E)-$C_{15}$-triphenylphosphonium salt, the 9-(Z) isomer in a content of 10–60%, in particular 30–55%, of the total weight of $C_{15}$-triphenylphosphonium salt. Direct use of this mother liquor for preparing 9-(Z)-retinoic acid is possible only with great difficulty.

SUMMARY OF THE INVENTION

It is an object of the present invention to develop a process with whose aid the desired 9-(Z)-retinoic acid can be prepared in a straightforward manner from the mother liquors of the $C_{15}$-triphenylphosphonium salt isolation.

DESCRIPTION OF THE PREFERRED EMBODIMENTS

We have found that this object is achieved by a process for preparing 9-(Z)-retinoic acid from mother liquors from the industrial preparation of $C_{15}$-triarylphosphonium salts of the formula I

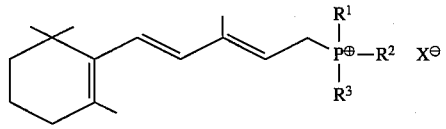

where $R^1$ to $R^3$ are each aryl, preferably phenyl, and X is halogen or $(HSO_4)$, in an organic solvent, which comprises A. increasing the proportion of 9-(Z)-$C_{15}$-triarylphosphonium salts in the $C_{15}$-triarylphosphonium salts which have been isolated from the mother liquors by extraction with water and concentration of the aqueous phase, by dissolving the oily $C_{15}$-triarylphosphonium salt mixture with heating in the minimum amount of a lower alkanol, preferably in isopropanol, and removing the all-(E)-$C_{15}$-triarylphosphonium salt which crystallizes out on cooling, B. reacting the resulting $C_{15}$-triarylphosphonium salt of the formula I which is enriched in the 9-(Z) isomer, in the presence of a base conventionally used in a Wittig reaction, in particular in the presence of an alkali metal or alkaline earth metal hydroxide, of an alkali metal or alkaline earth metal amide, of an alkali metal carbonate or of ammonia, in a solvent suitable for Wittig reactions, with an alkyl β-formylcrotonate of the general formula II

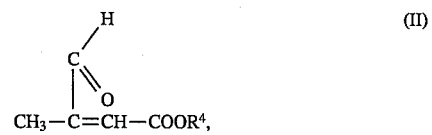

where $R^4$ is $C_1$–$C_4$-alkyl, and

C. hydrolyzing the above mixture of retinoic esters, which has been obtained by the conventional workup for Wittig reactions, in a $C_3$–$C_9$-alkanol, preferably in a propanol or a butanol, in particular in isobutanol, and precipitating the resulting 9-(Z)-retinoic acid as crystals from the alkanolic, preferably propanolic or butanolic, solution where appropriate by adding methanol, with the all-(E)-retinoic acid which is formed and other unknown retinoic acid isomers remaining in the alkanolic solution.

Particularly pure 9-(Z)-retinoic acid is obtained when the resulting 9-(Z)-retinoic acid is subsequently recrystallized from a butanol/methanol mixture, preferably an isobutanol/methanol mixture.

The process according to the invention takes place particularly advantageously when in step A the proportion of 9-(Z)-$C_{15}$-triarylphosphonium salt from the mother liquor from the $C_{15}$-triarylphosphonium salt preparation is isolated and increased by a) adding water to the mother liquor and separating off the organic phase, b) concentrating the aqueous phase under mild conditions, c) dissolving the resulting oil with heating in the minimum amount of isopropanol, d) separating off the all-(E)-$C_{15}$-triarylphosphonium salt which crystallizes out on cooling, and e) concentrating the resulting isopropanolic solution under mild conditions.

The $C_{15}$-triarylphosphonium salts are prepared in a conventional way, generally in solvents such as toluene, acetonitrile, xylene, decalin, methylene chloride, methyl tert-butyl ether, water and alkanols.

Accordingly, the mother liquors required for the process according to the invention are composed of one of these solvents or a mixture of solvents, triphenylphosphine oxide, hydrohalic acid or sulfuric acid and $C_{15}$-hydrocarbon as well as triarylphosphonium salts of the hydrohalic acid or sulfuric acid.

They contain, depending on the reaction conditions, the 9-(Z) isomer in an amount of 10–60%, preferably 30–55%, of the total amount of $C_{15}$-triarylphosphonium salts. The $C_{15}$-triarylphosphonium salts are extracted from this mother liquor with water, and the aqueous phase is concentrated under mild conditions. The resulting oil is taken up in an amount of a lower alkanol, preferably isopropanol, sufficient for the concentration of the salt to be 30–70% by weight, preferably 40–60% by weight, in particular 45–55% by weight. The resulting solution is then left to stand at from −50° to 25° C., preferably −30° to 0° C., when all-(E)-triarylphosphonium salt crystallizes out and can thus be separated off. After this enrichment of the 9-(Z)-$C_{15}$ salt, the ratio of 9-(Z)- to all-(E)-$C_{15}$-triphenylphosphonium salt in the mother liquor is from about 1:1 up to 50:1. In the example, a ratio of 90:6, corresponding to about 15:1, was obtained. A further enrichment of the 9-(Z) isomer is possible on the basis of kinetic control of the subsequent Wittig reaction because the remaining all-(E) isomer undergoes the Wittig reaction very much more quickly than the 9-(Z)-$C_{15}$-triarylphosphonium salt. This means that if the $C_{15}$-triarylphosphonium salt mixture is subjected to a Wittig reaction with an amount of aldehyde corresponding to the amount of all-(E)-$C_{15}$ salt still present, an acid workup of the reaction mixture permits, because of the kinetic differentiation, isolation of a 9-(Z)-$C_{15}$-triarylphosphonium salt.

A further advantage is displayed by the process according to the invention for preparing 9-(Z)-retinoic acid when, in step B, the $C_{15}$-triarylphosphonium salt of the general formula I, which has been enriched in the 9-(Z) isomer, is reacted in the presence of a base conventionally used for Wittig reactions, in particular in the presence of an alkali metal or alkaline earth metal hydroxide, of an alkali metal carbonate or of ammonia, in dimethylformamide, an alkanol/dimethylformamide mixture, an alkanol/water mixture, 1,4-dioxane, water or n-methylpyrrolidone, preferably in dimethylformamide, as solvent with the alkyl β-formylcrotonate of the general formula II. The Wittig reaction is otherwise carried out in a conventional way at from −30° to about +30° C., preferably from −10° C. to +10° C., in particular at about 0° C. For this purpose it is possible either to add the base to the two starting compounds in the solvent, or else to add the base to a solution of the $C_{15}$-triarylphosphonium salt and only then to add a solution of the alkyl β-formylcrotonate.

To carry out a particularly preferred type of Wittig reaction, lithium hydroxide is suspended in dimethylformamide (DMF) and the suspension is cooled to 0° C. To the cooled suspension is initially added slowly a solution of the $C_{15}$-triarylphosphonium salt in DMF and then slowly a solution of the β-formylcrotonic ester in DMF. The mixture is stirred at from +10° to −9° C., preferably +5° to −5° C., in particular +2° to −2° C., for 2–10, preferably 3–5, hours and then ice-water is added. The water/DMF phase is then extracted, for example, with a heptane/ethyl acetate mixture.

The organic phase is washed with water, and solvent is removed at about 40° C.

The base, in particular the lithium hydroxide, is used in amounts of from 2 to 6 mol, preferably 3 to 5 mol, per mol of $C_{15}$-triarylphosphonium salt for this purpose.

The solvent, in particular the DMF, is generally used in total amounts of from 2 to 8 liters (l), preferably 3 to 6 l, for each mol of $C_{15}$-triarylphosphonium salt.

The extractant which is advantageously used is heptane or a mixture of heptane and ethyl acetate. However, it is also possible to use all other organic solvents which are immiscible with water, such as ethers, aliphatic hydrocarbons, halogenated and aromatic hydrocarbons, to extract the mixture of alkyl retinoate isomers.

The solvents, in particular the DMF and the alkanols, substantially remain in the aqueous phase during this extraction and moreover keep the triphenylphosphine oxide which is formed in the Wittig reaction substantially in the aqueous phase.

It has proven advantageous when $C_{15}$-triarylphosphoniumhalides are used to carry out the Wittig reaction with the alkyl β-formylcrotonate of the general formula II in a 1,2-epoxyalkane having 3–6 carbon atoms, preferably in 1,2-epoxybutane or 1,2-epoxyhexane, and without adding one of the abovementioned bases conventional for Wittig reactions. In this case, the 1,2-epoxyalkanes eliminate hydrogen halide from the $C_{15}$-triarylphosphonium halides to form 2-haloalkanols and the corresponding $C_{15}$-triarylphosphoranes (cf. J. Buddrus in Angew. Chem. 80 (1968) 35–36). The latter then reacts with the alkyl β-formylcrotonate of the general formula II to give the corresponding alkyl retinoate. Thus, in this reaction the 1,2-epoxyalkane acts both as solvent and as base.

To carry out this process variant, the $C_{15}$-triarylphosphonium halide and the β-formylcrotonic ester are suspended in the 1,2-epoxyalkane, the suspension is slowly heated to about 35°–65° C., preferably 55°–65° C., and then stirred at this temperature for 2–24 hours, preferably 4–16 hours. After completion of the Wittig reaction, the epoxyalkane is removed from the reaction mixture by distillation under mild conditions.

The 1,2-epoxyalkane is used, like the other solvents, in amounts of about 2–8, preferably 3–6, l for each mol of $C_{15}$-triarylphosphonium halide.

The reaction mixture is worked up essentially as described above for the Wittig reaction in other solvents.

A further great advantage is achieved in the process according to the invention when, in step C, a) the resulting oily alkyl retinoate is dissolved in a propanol or a butanol, and b) hydrolyzed by heating with a 10–80% by weight, preferably a 15–60% by weight, in particular a 20–30% by weight, aqueous solution of an alkali metal or alkaline earth metal hydroxide, preferably an alkali metal hydroxide, c) retinoic acid is liberated by adding a mineral acid to the cooled alkaline reaction mixture, and d) 9-(Z)-retinoic acid is precipitated as crystals by adding methanol to the propanolic or butanolic solution.

With this type of ester cleavage, surprisingly, there are no disadvantageous effects on the isomer ratio. When $C_3$–$C_9$-alkanols, preferably propanols and butanols, in particular isobutanol, are used as solvents for the ester cleavage it is possible to precipitate the 9-(Z)-retinoic acid particularly advantageously in the form of pale orange crystals by adding a lower alkanol, in particular a methanol, while all-(E)-retinoic acid or other retinoic acid isomers remain in solution. Alternatively, the concentration of 9-(Z)-retinoic ester in the alkanol in the hydrolysis process can be adjusted so that it is possible to crystallize 9-(Z)-retinoic acid directly out of the reaction mixture even without adding methanol.

With the aid of the process according to the invention it is possible for the first time to obtain 9-(Z)-retinoic acid in a relatively straightforward manner and without using elaborate chromatographic purification methods in the final stage. It is particularly advantageous that it is possible to utilize the mother liquors produced in the industrial preparation of $C_{15}$-triarylphosphonium salts, which it has hitherto been necessary to dispose of. Enrichment of the 9-(Z)-$C_{15}$-triarylphosphonium salt can be achieved relatively straightforwardly according to the invention, which makes it possible to isolate without difficulty the 9-(Z)-retinoic acid in the final stage of the process according to the invention in the specific solvent system.

The following examples are intended to illustrate the procedure for the process according to the invention.

The following conditions were chosen for the HPLC analyses:

a) $C_{15}$-Triphenylphosphonium salt: Nucleosil 120, 7 μm, RP-18, 1 ml/min, 220 nm, methanol/water =7:3+0.04% of cetylammonium bromide, pH=2.0 b) Retinoic acid: Lichrosorb, 5 μm, RP-18, 1.2 ml/min, 352 nm, methanol/water/acetic acid=80:20:0.5

EXAMPLE 1

Preparation of 9-(Z)-retinoic acid

A. Enrichment of 9-(Z)-$C_{15}$-triphenylphosphonium salt 1 liter of a mother liquor from the preparation of 3-methyl-5-(2,6,6-trimethyl-1-cyclohexen-1-yl)-2,4-pentadienyl-triphenylphosphonium bisulfate ($C_{15}$-triphenylphosphonium sulfate) in heptane/isopropanol was vigorously mixed with 250 ml of water. After removal of the organic phase, the aqueous solution was completely evaporated in a rotary evaporator at 90° C. 91.8 g of a pale brown oil were obtained and, according to HPLC analysis, comprised about 38% 9-(Z)- and 53% all-(E)-$C_{15}$-triphenylphosphonium sulfate. This oil was taken up in 120 ml of isopropanol to result in an approximately 50% by weight solution. The solution was then left to stand in a refrigerator overnight, the crystals which had separated out were filtered off, and the solution was evaporated in a rotary evaporator. 42.2 g of a pale brown oil were obtained and, according to HPLC analysis, comprised about 65.8% 9-(Z)-$C_{15}$-triphenylphosphonium bisulfate and 19% all-(E)-$C_{15}$-triphenylphosphonium bisulfate.

B. Wittig reaction with methyl β-formylcrotonate 9 g (0.37 mol) of LiOH were suspended in 100 ml of dimethylformamide (DMF) and cooled to 0° under $N_2$ protective gas. Subsequently a solution of 39.6 g (0.0704 mol) of the $C_{15}$-triphenylphosphonium salt obtained as in A. in 100 ml of DMF was added dropwise at 0° C. to the LiOH suspension over the course of 30 minutes (min). Subsequently a solution of 14.5 g (0.113 mol) of methyl β-formylcrotonate in 70 ml of DMF was added over the course of 30 min.

The mixture was stirred at 0° C. for 4 hours and then 400 ml of ice-water were added. The water/DMF phase was then extracted 3 times with 180 ml of a heptane/ethyl acetate (2/1) mixture. The resulting organic phase was washed twice with 100 ml of water each time and then concentrated in a rotary evaporator to result in 17.85 g of a brown oil.

C. Isolation of 9-(Z)-retinoic acid 17.85 g of the retinoic ester mixture obtained as in B. were taken up in 50 ml of isobutanol, 12.5 g of a 25% by weight aqueous NaOH were added, and the reaction mixture was initially kept at 80° C. for 75 min and then cooled to 60° C., and 38 ml of a 10% by weight aqueous sulfuric acid were added. After phase separation, 40 ml of methanol were added to the isobutanol phase, when 9-(Z)-retinoic acid crystallized out immediately. The crystals were filtered off and then washed twice with 50 ml of methanol (−30° C.) each time. 4 g of 9-(Z)-retinoic acid were obtained. This corresponds to a yield of 32% based on the 9-(Z)-$C_{15}$-triphenylphosphonium bisulfate present in the mother liquor from $C_{15}$ salt production.

The alcoholic mother liquor (13.5 g) resulting after the isolation of 9-(Z)-retinoic acid comprises, according to HPLC analysis, 35% all-(E)-retinoic acid, 17.2% 9-(Z)-retinoic acid and 34% unknown retinoic acid isomers.

D. Recrystallization of 9-(Z)-retinoic acid 5.2 g of a 9-(Z)-retinoic acid prepared as in A. to C. (purity 94.3%) were stirred in 80 ml of an isobutanol/methanol mixture (1/1) at 80° C. for 10 min. The mixture was then cooled to 0° C. 9-(Z)-retinoic acid crystallized out over the course of one hour, and was filtered off and washed with 50 ml of methanol (−30° C.). 4.0 g of 9-(Z)-retinoic acid with a purity of 99.5% were obtained.

EXAMPLE 2

A. Enrichment of 9-(Z)-$C_{15}$-triphenylphosphonium halide 1 liter of a mother liquor from the preparation of 3-methyl-5-(2,6,6-trimethyl-1-cyclohexen-1-yl)-2,4-pentadienyl-triphenylphosphonium chloride in heptane/isopropanol was vigorously mixed with 300 ml of water. After removal of the organic phase, the aqueous solution was completely evaporated in a rotary evaporator at 80° C. 102 g of a pale brown oil were obtained and, according to HPLC analysis, comprised about 42% 9-(Z)- and 44% all-(E)-$C_{15}$-triphenylphosphonium chloride. This oil was taken up in 150 ml of isopropanol to result in an approximately 50% by weight solution. The solution was then left to stand in a refrigerator overnight, the crystals which had separated out were filtered off, and the solution was evaporated in a rotary evaporator. A pale brown oil was obtained and comprised, according to HPLC analysis, about 63% 9-(Z)-$C_{15}$-triphenylphosphonium chloride.

B. Wittig reaction in 1,2-epoxybutane 50.05 g (0.1 mol) of the $C_{15}$-triphenylphosphonium chloride obtained as in Example 2A. were suspended in 500 ml of 1,2-epoxybutane, and 14.1 g (0.11 mol) of methyl β-formylcrotonate were added to this suspension at 25° C., and then the mixture was heated over the course of 1 h to the reflux temperature of 65° C. and finally refluxed for a further 12 h. Then excess 1,2-epoxybutane was removed by distillation at 40° C./150–200 mbar, and the residue was mixed and extracted with 250 ml of a hexane/ethyl acetate mixture (1:1) and 250 ml of water at 5° C. The resulting organic phase was washed twice with 100 ml of water each time and then concentrated at 30° C./20 mbar, resulting in 19.2 g of a brownish oil. The 9-(Z) content in the resulting methyl retinoate mixture was 37–41% by weight according to HPLC analysis.

C. The isolation and purification of 9-(Z)-retinoic acid took place as in Examples 1C and 1D.

EXAMPLE 3

Wittig reaction in 1,2-epoxyhexane 25 g (0.046 mol) of a $C_{15}$-triphenylphosphoniumbromide obtained as in Example 2A. were mixed with 250 ml of 1,2-epoxyhexane and 9.6 g (0.075 mol) of methyl β-formylcrotonate, and the mixture was heated to 62° C. over the course of 2 h and then stirred at this temperature for 10 h. Subsequently excess 1,2-epoxyhexane (boiling point 116°–120° C.) was removed by distillation at 60° C./50–100 mbar, and the residue was mixed and extracted with 100 ml of heptane, 100 ml of ethyl acetate and 200 ml of a 2% by weight aqueous sodium carbonate solution at 5° C. The resulting aqueous phase was extracted twice more with 150 ml of a heptane/methyl acetate mixture (2:1) each time. The combined organic phases were washed three times with water and then concentrated at 30° C./20 mbar. 8.5 g of a brownish oil were obtained and were converted as in Example 1 C and 1 D into pure 9-(Z)-retinoic acid.

We claim:

1. A process for preparing 9-(Z)-retinoic acid from mother liquors from the industrial preparation of $C_{15}$-triarylphosphonium salts of the formula I

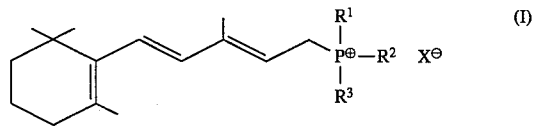

where $R^1$ to $R^3$ are each aryl, and X is halogen or ($HSO_4$), in an organic solvent, which comprises A. increasing the proportion of 9-(Z)-$C_{15}$-triarylphosphonium salts in the $C_{15}$-triarylphosphonium salts which have been isolated from the mother liquors by extraction with water and concentration of the aqueous phase, by dissolving the oily $C_{15}$-triarylphosphonium salt mixture with heating in the minimum amount of a lower alkanol and removing the all-(E)-$C_{15}$-triarylphosphonium salt which crystallizes out on cooling, B. reacting the resulting $C_{15}$-triarylphosphonium salt of the formula I which is enriched in the 9-(Z) isomer in a ratio of 9-(Z)- to all-(E)-$C_{15}$-triarylphosphonium salt of from about 1:1 to 50:1, in the presence of an alkali metal or alkaline earth metal hydroxide, of an alkali metal or alkaline earth metal amide, of an alkali metal carbonate or of ammonia, in a solvent suitable for Wittig reactions, with an alkyl β-formylcrotonate of the formula II

where $R^4$ is $C_1$–$C_4$-alkyl, and

C. hydrolyzing the above mixture of retinoic esters, which has been obtained by the conventional workup for Witting reactions, in a $C_3$–$C_9$-alkanol and precipitating the resulting 9-(Z)-retinoic acid as crystals from the alkanolic solution where appropriate by adding methanol, with the all-(E)-retinioic acid which is formed and other unknown retinoic acid isomers remaining in the alkanolic solution.

2. A process for preparing 9-(Z)-retinoic acid as defined in claim 1, wherein in step A the oily $C_{15}$-triarylphosphonium salt mixture is dissolved in isopropanol as lower alkanol.

3. A process as defined in claim 1, wherein the resulting 9-(Z)-retinoic acid is subsequently recrystallized from a butano/methanol mixture.

4. A process for preparing 9-(Z)-retinoic acid as defined in claim 1, wherein in step A the proportion of 9-(Z)-$C_{15}$-triarylphosphonium salt from the mother liquor from the $C_{15}$-triarylphosphonium salt preparation is isolated and increased by a) adding water to the mother liquor and separating off the organic phase, b) concentrating the aqueous phase under mild conditions, c) dissolving the resulting oil with heating in the minimum amount of isopropanol, d) separating off the all-(E)-$C_{15}$-triarylphosphonium salt which crystallizes out on cooling, and e) concentrating the resulting isopropanolic solution under mild conditions.

5. A process for preparing 9-(Z)-retinoic acid as defined in claim 1, wherein in step B the $C_{15}$-triarylphosphonium salt of the general formula I, which has been enriched in the 9-(Z) isomer, is reacted in the presence of an alkali metal or alkaline earth metal hydroxide, of an alkali metal carbonate or of ammonia, in a solvent selected from the group consisting of dimethylformamide, an alkanol/dimethylformamide mixture, an alkanol/water mixture, 1,4-dioxane, water and n-methylpyrrolidone with the alkyl β-formylcrotonate of the formula II.

6. A process as defined in claim 5, wherein the $C_{15}$-triarylphosphonium salt of the formula I which is enriched in the 9-(Z) isomer is reacted with the alkyl β-formylcrotonate of the general formula II in dimethylformamide or 1,4-dioxane as solvent.

7. A process for preparing 9-(Z)-retinoic acid as defined in claim 1, wherein in step B the $C_{15}$-triarylphosphonium salt of the general formula I which is enriched in the 9-(Z) isomer and in which $R^1$ to $R^3$ are each aryl and X is halogen is reacted in a 1,2-epoxyalkane with 3 to 6 carbon atoms and without adding significant amounts of one of the bases conventional for Wittig reactions with the alkyl β-formylcrotonate of the general formula II.

8. A process for preparing 9-(Z)-retinoic acid as defined in claim 1, wherein in step C the resulting retinoic ester mixture is hydrolyzed in a propanol or a butanol and the resulting 9-(Z)-retinoic acid is precipitated from the propanolic or butanolic solution with methanol.

9. A process for preparing 9-(Z)-retinoic acid as defined in claim 1, wherein in step C a) the resulting oily alkyl retinoate is dissolved in a butanol, and b) hydrolyzed by heating with a 10–80% by weight aqueous solution of an alkali metal or alkaline earth metal hydroxide, c) retinoic acid is liberated by adding a mineral acid to the cooled alkaline reaction mixture, and d) 9-(Z)-retinoic acid is precipitated as crystals by adding methanol to the butanolic solution.

10. The process of claim 1, wherein in step A a mother liquor of the industrial preparation of $C_{15}$-triarylphosphonium salts of the formula I is used, in which the 6-(Z)-isomer is contained in an amount of 10–70% of the total amount of $C_{15}$-triarylphosphonium salts.

11. The process of claim 1, wherein in step A after the enrichment of the 9-(Z)-$C_{15}$ salt, the ratio of 9-(Z)- to all-(E)-$C_{15}$-triphenylphosphonium salt is from about 1:1 to 50:1.

12. The process of claim 1, wherein in step A the $C_{15}$-triarylphosphonium salts, which have been isolated from the mother liquors by extraction with water and concentration of the aqueous phase were dissolved in isopropanol, sufficient for the concentration of the salt to be 30–70% by weight and the resulting solution is then left to stand at from −50° to 25° C. until most of the all-(E)-triarylphosphonium salt is crystallized out and can thus be separated off.

13. A process for increasing the 9-(Z) proportion in mother liquors from the industrial preparation of $C_{15}$-triarylphosphonium salts of the formula I

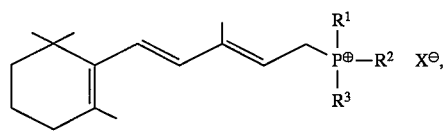

where $R^1$ to $R^3$ are each aryl and X is halogen or ($HSO_4$), in an organic solvent, which comprises dissolving the $C_{15}$-triarylphosphonium salt which has been isolated from the mother liquors by extraction with water and concentration of the aqueous phase, with heating in the minimum amount of a lower alkanol, and separating off the all-(E)-triarylphosphonium salt which crystallizes out on cooling.

* * * * *

UNITED STATES PATENT AND TRADEMARK OFFICE
CERTIFICATE OF CORRECTION

PATENT NO.: 5,504,230

DATED: April 2, 1996

INVENTOR(S): JOHN et al.

It is certified that error appears in the above-identified patent and that said Letters Patent is hereby corrected as shown below:

Column 8, claim 10, line 32, "6-(Z)-isomer" should be --9-(Z)-isomer--.

Signed and Sealed this

Thirtieth Day of July, 1996

Attest:

BRUCE LEHMAN

*Attesting Officer*  *Commissioner of Patents and Trademarks*